(12) United States Patent
Benkhoff et al.

(10) Patent No.: US 7,144,993 B2
(45) Date of Patent: Dec. 5, 2006

(54) PROCESS FOR THE PREPARATION OF 4-METHYL-7-AMINOQUINOLONES

(75) Inventors: Johannes Benkhoff, Basel (CH); Bernd Lamatsch, Riehen (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 232 days.

(21) Appl. No.: 10/498,456

(22) PCT Filed: Dec. 3, 2002

(86) PCT No.: PCT/EP02/13663

§ 371 (c)(1),
(2), (4) Date: Jun. 8, 2004

(87) PCT Pub. No.: WO03/050089

PCT Pub. Date: Jun. 19, 2003

(65) Prior Publication Data

US 2005/0222397 A1    Oct. 6, 2005

(30) Foreign Application Priority Data

Dec. 11, 2001  (EP)  ................. 01811206

(51) Int. Cl.
C07D 215/38     (2006.01)
C07C 235/80     (2006.01)
(52) U.S. Cl. ............... 534/740; 534/768; 534/771; 546/153; 562/53; 564/200
(58) Field of Classification Search ........... 534/740, 534/768, 771; 546/153; 562/53; 564/220
See application file for complete search history.

(56) References Cited

U.S. PATENT DOCUMENTS

| | | | |
|---|---|---|---|
| 2,152,786 A * | 4/1939 | Boese, Jr. ................ | 564/155 |
| 2,311,054 A * | 2/1943 | Kenyon et al. ........... | 564/200 |
| 2,688,543 A * | 9/1954 | Von Glahn et al. ....... | 430/146 |
| 2,936,306 A | 5/1960 | Schmid et al. ........... | 260/176 |
| 3,119,808 A | 1/1964 | Buckley et al. .......... | 260/155 |
| 3,304,328 A | 2/1967 | Pelley ..................... | 260/562 |
| 3,907,494 A | 9/1975 | Saygin .................... | 8/10 |
| 3,933,886 A | 1/1976 | Saygin .................... | 260/465 |
| 4,039,316 A | 8/1977 | Perronnet et al. ......... | 71/118 |
| 4,064,131 A | 12/1977 | Herkenrath .............. | 260/287 |

FOREIGN PATENT DOCUMENTS

GB  1541460    2/1979
JP  62-215560  * 9/1987

OTHER PUBLICATIONS

R. M. Forbis et al., Journal of the American Chemical Society, 95:15, Jul. 1973, pp. 5003-5013.

A. Guiotto et al., J. Heterocyclic Chem., vol. 26, Jul. 1989, pp. 917-922.
L. Monti, Gazz. Chim. Ital., vol. 70,(1940), pp. 648-656.
P. López-Alverado et al., Synthesis, (1998), pp. 186-194.

* cited by examiner

Primary Examiner—Fiona T. Powers
(74) Attorney, Agent, or Firm—Tyler A. Stevenson

(57) ABSTRACT

The present invention relates to a process for the preparation of a compound of the general formula (I), which comprises converting a compound of the general formula (II), in an aprotic organic solvent in the presence of a catalytically active amount of a strong acid (catalyst) or of an agent that liberates a strong acid or of an ammonium salt of a strong acid, it also being possible for the catalyst to be part of the starting material/product, into a compound of formula I, wherein $R^5$, $R^6$ and $R^8$ are each independently of the others a hydrogen atom, a nitro group, a sulfo group, a halogen atom, a pseudohalogen, a group $COOR^1$ or $CONHR^2$ or a $C_{1-8}$ alkyl, $C_{1-8}$ alkoxy or aryloxy radical, an amide group, a thioalkyl or thioaryl radical, an alkyl- or aryl-sulfonyl radical, an alkyl- or aryl-sulfinyl radical, a trifluoromethyl group or a phosphono group, $R^1$ and $R^2$ being a hydrogen atom or a $C_{1-8}$ alkyl radical or an aryl or aralkyl radical, $R^{10}$ is a group $-C(O)CH_2C(O)CH_3$ and $R^{11}$ is a hydrogen atom or an acyl radical, or $R^{10}$ and $R^{11}$ are a group $-C(O)CH_2C(O)CH_3$. The process according to the invention is simple to perform and results in products of high chemical purity and high isomeric purity in a high yield

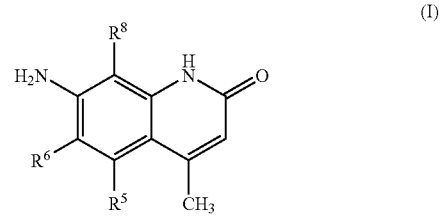

(I)

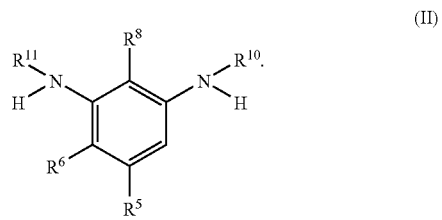

(II)

11 Claims, No Drawings

PROCESS FOR THE PREPARATION OF 4-METHYL-7-AMINOQUINOLONES

The present invention relates to a process for the preparation of 4-methyl-7-aminoquinolones of formula (I). The process according to the invention is simple to perform and results in products of high chemical purity and high isomeric purity in a high yield.

Processes for the preparation of 4-methyl-6-chloro-7-aminoquinolones are known:

U.S. Pat. No. 3,119,808 describes, for example, the synthesis of 4-methyl-6-chloro-7-amino-quinolone. First of all, 1 mol of 4-chloro-m-phenylenediamine in toluene is reacted with 2 mol of diketene. The crystalline precipitate of the N,N-diacetoacetyl product is then converted into 4-methyl-6-chloro-7-aminoquinolone by heating in aqueous hydrochloric acid.

According to DE-A-95 86 47, 4-methyl-6-chloro-7-aminoquinolone is obtained by first reacting 4-chloro-m-phenylenediamine in water with diketene and then converting the resulting oily acetoacetyl compound into 4-methyl-6-chloro-7-aminoquinolone by heating in the presence of sulfuric acid.

Furthermore, DE-A-24 44 519 describes a process for the preparation of 1,2-dihydro-2-oxo-4-methylquinoline derivatives of formula

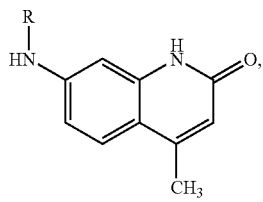

in which R is a hydrogen atom or a group —C(O)CH$_2$C(O)CH$_3$, wherein 1 mol of m-phenylenediamine is reacted with 1 mol or 2 mol, respectively, of diketene in an organic solvent, such as methanol, butyl acetate, carbon tetrachloride or toluene, with the addition of about 5% glacial acetic acid or in glacial acetic acid at temperatures of below 100° C.

The processes described above do not proceed uniformly, that is to say large amounts of secondary products are formed which have to be separated off by recrystallisation of the reaction product. For example, in the case of the procedure described in DE-A-95 86 47, in addition to the desired product, 4-methyl-6-chloro-7-aminoquinolone, there is formed the undesired isomer, 4-methyl-5-amino-6-chloro-quinolone, in amounts of about 14%.

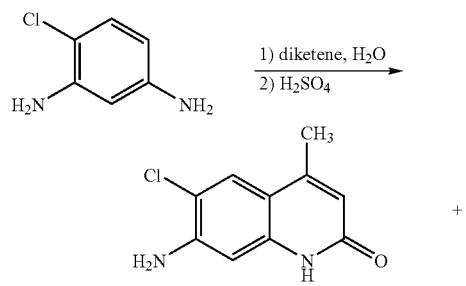

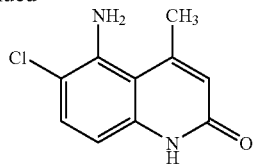

The aim of the present invention is therefore to provide a process for the preparation of 7-aminoquinolinones, especially 4-methyl-6-chloro-7-aminoquinolone, that is simple to perform and results in a product of high chemical purity and high isomeric purity in a high yield.

That aim is achieved by a process for the preparation of a compound of the general formula

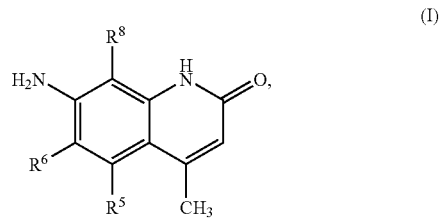

which comprises converting a compound of the general formula

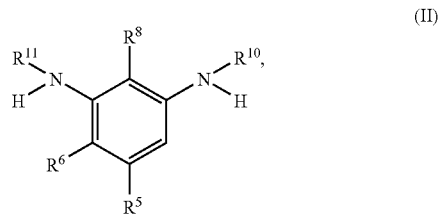

in an aprotic organic solvent in the presence of a catalytically active amount of a strong acid or of an agent that liberates a strong acid or of an ammonium salt of a strong acid, it also being possible for the catalyst to be part of the starting material/product, into a compound of formula I, wherein $R^5$, $R^6$ and $R^8$ are each independently of the others a hydrogen atom, a nitro group, a sulfo group, a halogen atom, a pseudohalogen, a group COOR$^1$ or CONHR$^2$, a $C_{1-8}$alkyl, $C_{1-8}$alkoxy or aryloxy radical, an amide group, a thioalkyl or thioaryl radical, an alkyl- or aryl-sulfonyl radical, an alkyl- or aryl-sulfinyl radical, a trifluoromethyl group or a phosphono group, $R^1$ and $R^2$ being a hydrogen atom or a $C_{1-8}$alkyl radical or an aryl or aralkyl radical, $R^{10}$ is a group —C(O)CH$_2$C(O)CH$_3$ and $R^{11}$ is a hydrogen atom or an acyl radical, or $R^{10}$ and $R^{11}$ are a group —C(O)CH$_2$C(O)CH$_3$.

Depending upon the substitution pattern, the reaction conditions for the conversion of compounds of formula II into compounds of formula I may vary. The conversion of a compound of formula II into a compound of formula I is generally carried out at a temperature of from 20 to 200° C., especially from 90 to 130° C.

According to the present invention, aprotic solvents are to be understood as being solvents having a pKa value greater than 17.

The aprotic organic solvent is generally selected from open-chain or cyclic amides, for example N,N-dimethylformamide (DMF), N,N-dimethylacetamide (DMA), N-methyl-pyrrolidone (NMP), dimethyl sulfoxide (DMSO), amines, such as primary, secondary and tertiary alkylamines, such as di-n-butylamine, cycloarylamines, especially pyridine and alkylpyridines, such as 2-, 3- or 4-methylpyridine, and alkylarylamines, cycloalkylamines, such as piperazine, piperidine, morpholine and N-alkylated derivatives thereof, open-chain or cyclic esters, for example n-butyl acetate, γ-butyrolactone or 1,2-propylene carbonate, butyronitrile, diphenyl ether, ethers, especially those having from 2 to 8 carbon atoms, for example diethyl ether, methyl ethyl ether, di-n-propyl ether, diisopropyl ether, methyl n-butyl ether, methyl tert-butyl ether, ethyl n-propyl ether, di-n-butyl ether, tetrahydrofuran, 1,4-dioxane, 1,2-dimethoxyethane, bis-β-methoxyethyl ether; aliphatic hydrocarbons, for example hexane, heptane, low- and high-boiling petroleum ethers; cycloaliphatic hydrocarbons, for example cyclohexane, methylcyclohexane, decahydronaphthalene; aromatic hydrocarbons, for example benzene, toluene, o-, m- and p-xylene, ethylbenzene, 1,2,3,4-tetrahydronaphthalene, and also commercially available aromatic solvents and solvent mixtures, which are marketed, for example, by Shell Chemical under the trade name Shellsol® and by Deutsche EXXON CHEMICAL GmbH under the trade name Solvesso®, such as Solvesso® 100, Solvesso® 150, Solvesso 200® (aromatic $C_{10}$–$C_{13}$ hydrocarbon solvent), SHELLSOL A100® (aromatic $C_9$–$C_{10}$ hydrocarbon solvent) or SHELLSOL A150® (aromatic $C_{10}$–$C_{11}$ hydrocarbon solvent), mixtures of aromatic hydrocarbons with ethers, such as the eutectic mixture of biphenyl and diphenyl ether marketed by Dow Chemicals under the trade name Dowtherm® A; halogenated aliphatic or aromatic hydrocarbons, for example methylene chloride, chloroform, carbon tetrachloride, chlorobenzene and dichlorobenzene; and mixtures of such solvents, most preference being given to aliphatic ethers, such as dibutyl ether, aromatic hydrocarbons, such as toluene, Solvesso® 150 or 1,2,3,4-tetrahydronaphthalene, aliphatic hydrocarbons, such as benzine (boiling range 110–140° C.) or deca-hydronaphthalene, mixtures of aromatic hydrocarbons with ethers, such as Dowtherm® A, and open-chain or cyclic esters, such as 1,2-propylene carbonate or n-butyl acetate, toluene, and di-n-butyl ether.

The conversion of a compound of formula II into a compound of formula I can be carried out in the presence of strong anhydrous inorganic acids, for example hydrogen chloride, hydrogen bromide, phosphoric acid, phosphorous acid (phosphonic acid), sulfuric acid, sulfamic acid, $NaHSO_4$, perchloric acid, boric acid, tetrafluoroboric acid and acid salts thereof, for example hydrogen carbonate and sulfate, inorganic solid acids, such as zeolites, silicates and argillaceous earths, and also Lewis acids, for example $AlCl_3$, $FeCl_3$, $ZnCl_2$, the trifluoromethanesulfonates of elements of sub-group III and of the lanthanoids, such as scandium(III) trifluoromethanesulfonate, yttrium(III) trifluoromethanesulfonate and ytter-bium(III) trifluoromethanesulfonate, in the presence of strong organic acids, for example halocarboxylic acids, such as mono-, di- and tri-haloacetic acids, such as monochloro-, trifluoro- and trichloro-acetic acid, sulfonic acids, that is to say organic derivatives (aromatic, aliphatic, cycloaliphatic) of sulfuric acid having the radical —$SO_3H$ as functional group, such as methanesulfonic acid, tert-butylsulfonic acid, tert-octylsulfonic acid, tert-dodecyl-sulfonic acid, n-cyclohexylsulfamic acid, benzenesulfonic acid, p-toluenesulfonic acid or amino-benzenesulfonic acid, dodecylbenzenesulfonic acid, mesitylsulfonic acid, 2,4,6-triisopropyl-benzenesulfonic acid or organic phosphonic acids, that is to say organic derivatives of phosphonic acid having a P—C bond, for example phenylphosphonic acid or p-toluene-phosphonic acid. Strong organic acids and ammonium salts thereof may also be polymer-bonded acids, for example perfluorinated resin sulfonic acids, such as poly (perfluoroalkene-sulfonic acids), such as Nafion®, and salts, such as polyvinylpyridinium toluenesulfonate. Especially preferred are p-toluenesulfonic acid and pyridinium p-toluenesulfonate (PPTS) and dodecylbenzenesulfonic acid, or ammonium salts, especially pyridinium salts, of strong organic or inorganic acids.

Ammonium salts of strong organic acids, in addition to being salts with $NH_4^+$, are to be understood as being also salts derived from primary, secondary and tertiary ammonium cations, it also being possible for the tetravalent nitrogen to be a member of a 5- or 6-membered ring, which may contain additional hetero atoms, such as S, N and O. Examples of such ammonium cations are compounds of formula

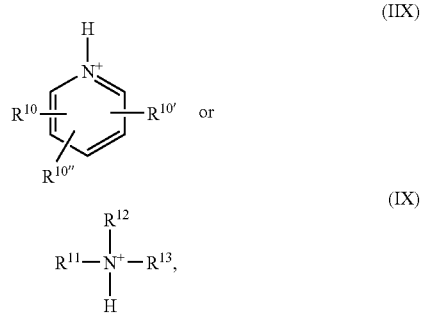

wherein $R^{10}$, $R^{10'}$ and $R^{10''}$ are each independently of the others a hydrogen atom or a straight-chain or branched $C_{1-8}$alkyl radical, $R^{11}$, $R^{12}$ and $R^{13}$ are a hydrogen atom, a straight-chain or branched $C_{1-8}$alkyl radical, a $C_{5-7}$cycloalkyl radical unsubstituted or substituted by from one to three $C_{1-4}$alkyl radicals, such as cyclohexyl or 3,3,5-trimethylcyclohexyl, or an aryl or aralkyl radical, preference being given to pyridinium salts and also to 2,6-lutidinium, 2,4,6-collidinium, 2,6-di-tert-butylpyridinium, 2,6-di-tert-butyl-4-methylpyridinium, 2,4,6-tri-tert-butylpyridinium and 2,6-diphenylpyridinium salts. It is also possible for a plurality of pyridine rings to be linked to one another. Examples of such compounds are 4,4'-bipyridinium salts, preference being given to 2,2'-bipyridinium and 2,2':6',2''-terpyridinium salts.

$R^{10}$, $R^{10'}$ and $R^{10''}$ together can also form aromatic, heteroaromatic, aliphatic and hetero-aliphatic ring systems. Examples of such ring systems are quinolinium and tetrahydro-quinolinium salts. 1,10-Phenanthrolinium and 2,2'-diquinolylium salts are preferred. The ammonium salt of the strong organic acid can also be part of the starting material or product.

Furthermore, the conversion of a compound of formula II into a compound of formula I can be carried out in the presence of an agent which liberates a strong inorganic or organic acid under the reaction conditions used, for example in the presence of water, e.g. the residual water present in the solvent. Examples of agents that liberate strong inorganic or organic acid are the SO$_3$/pyridine complex, acid halides or symmetric or asymmetric anhydrides of inorganic acids, for example P$_2$O$_5$, SO$_3$, POCl$_3$, SOCl$_2$, PCl$_3$ or PCl$_5$, or organic acids, such as sulfonic acids, such as mesyl chloride, tosyl chloride or tosyl anhydride, or carboxylic acids, such as 2,4,6-trimethylbenzoyl chloride or benzoyl chloride. Preference is given to acid halides and anhydrides of the strong organic acids mentioned above.

The catalyst can likewise be part of the starting material/product. Examples of such catalysts are compounds of formula I or II in which at least one of the substituents R$^5$, R$^6$ and R$^8$ is a sulfonic acid group (sulfo group) or a salt of a sulfonic acid group (see Example 3).

According to the invention a strong organic or inorganic acid is to be understood as being an acid having a pK$_a$ value of less than 2.5 and also iodine.

The following catalysts are especially preferred:
pyridinium p-toluenesulfonate (PPTS), pyridinium dodecylbenzenesulfonate, pyridinium tetra-fluoroborate, pyridinium hydrogen sulfate, pyridine/SO$_3$ complex,

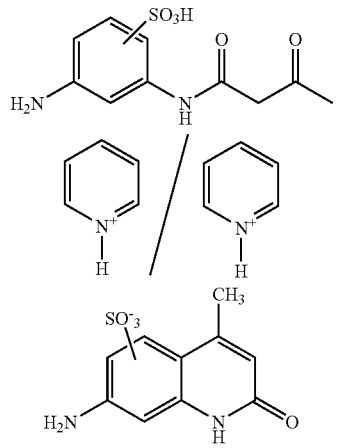

p-toluenesulfonic acid, benzenesulfonic acid, dodecylbenzenesulfonic acid, p-toluenesulfonic acid chloride, p-toluenesulfonic anhydride, benzoyl chloride, 2,4,6-trimethylbenzoyl chloride, sulfuric acid, amidosulfuric acid (sulfamic acid), sodium hydrogen sulfate, anhydrous zinc chloride, anhydrous iron(III) chloride, anhydrous aluminium chloride, scandium(III) trifluoromethanesulfonate, yttrium(III) trifluoromethanesulfonate, ytterbium(III) trifluoromethanesulfonate, iodine.

The acids are used in catalytically active amounts. When the catalyst is not part of the starting material or product, the catalytically active amount of the acid is generally from 0.1 to 20% by weight, preferably from 5 to 15% by weight, based on the compound of formula II. When the catalyst (for example in the form of a sulfonic acid group, ammonium salt of a sulfonic acid group or in the form of a group that liberates a sulfonic acid group) is part of the starting material or product, the amount of catalyst corresponds to the amount of starting material used.

Products of high isomeric purity and high chemical purity are obtained especially when anhydrous solvents and reagents are used, the isomeric purity and chemical purity being further increased if the water formed during the reaction is Immediately withdrawn from the reaction equilibrium, for example by distillative removal of the water of reaction.

The process according to the invention is especially suitable for the preparation of compounds of formula I in which R$^8$ is a hydrogen atom or in which R$^6$ is a halogen atom or pseudohalogen, especially a chlorine atom, or a sulfo group and R$^5$ and R$^8$ are a hydrogen atom.

According to the invention a C$_{1-8}$alkyl radical is to be understood as being a straight-chain or branched alkyl radical, for example methyl, ethyl, n-propyl, Isopropyl n-butyl, sec-butyl, isobutyl, tert-butyl, n-pentyl, 2-pentyl, 3-pentyl, 2,2-dimethylpropyl, hexyl, heptyl, 2,4,4-tri-methylpentyl, 2-ethylhexyl or octyl, preference being given to a C$_{1-4}$alkyl radical.

According to the invention a C$_{1-8}$alkoxy radical is to be understood as being a straight-chain or branched O—C$_{1-8}$alkyl radical, preferably a O—C$_{1-4}$alkyl radical, for example methoxy, ethoxy, n-propoxy, isopropoxy, n-butoxy, sec-butoxy, isobutoxy, tert-butoxy, n-pentyloxy, 2-pentyloxy, 3-pentyloxy, 2,2-dimethylpropoxy, n-hexyloxy; n-heptyloxy, n-octyloxy, 1,1,3,3-tetramethylbutoxy or 2-ethylhexyloxy.

According to the invention an acyl radical is to be understood as being a C$_{2-18}$acyl radical, preferably a C$_{2-8}$acyl radical, for example acetyl, propionyl, butanoyl or benzoyl.

According to the invention an aryl radical is to be understood as being a C$_{6-24}$aryl radical, preferably a C$_{6-12}$aryl radical, which may be unsubstituted or substituted by C$_{1-4}$alkyl or by C$_{1-4}$alkoxy, for example phenyl, 4-methylphenyl, 4-methoxyphenyl or naphthyl.

According to the invention an aralkyl radical is to be understood as being a C$_{7-24}$aralkyl radical, preferably a C$_{7-12}$aralkyl radical, which may be unsubstituted or substituted by from one to three C$_{1-4}$alkyl radicals, for example benzyl, 2-benzyl-2-propyl, β-phenyl-ethyl, α,α-dimethylbenzyl or ω-phenyl-butyl.

According to the invention an aryloxy radical is to be understood as being a C$_{6-24}$aryloxy radical, preferably a C$_{6-12}$aryloxy radical, for example phenoxy or 4-methylphenoxy.

According to the invention an amide group is to be understood as being an acylated nitrogen atom, for example an acetamido, benzamido or 4-chlorobenzamido group.

According to the invention a thioalkyl radical is to be understood as being a sulfur atom substituted by an alkyl group, alkyl being understood in the above sense, for example a methylmercapto, ethylmercapto or tert-butylmercapto group.

According to the invention a thioaryl radical is to be understood as being a sulfur atom substituted by an aryl group, aryl being understood in the above sense, for example a phenylmercapto, 4-methylphenylmercapto or naphthylmercapto group.

According to the invention an alkylsulfonyl radical is to be understood as being an alkyl group bonded by way of a SO$_2$ unit, alkyl being understood in the above sense, for example a methylsulfonyl, ethylsulfonyl or tert-butylsulfonyl group.

According to the invention an arylsulfonyl radical is to be understood as being an aryl group bonded by way of a SO$_2$ unit, aryl being understood in the above sense, for example a phenylsulfonyl, 4-methylphenylsulfonyl or naphthylsulfonyl group.

According to the invention an alkylsulfinyl radical is to be understood as being an alkyl group bonded by way of a SO unit, alkyl being understood in the above sense, for example a methylsulfinyl, ethylsulfinyl or tert-butylsulfinyl group.

According to the invention an arylsulfinyl radical is to be understood as being an aryl group bonded by way of a SO unit, aryl being understood in the above sense, for example a phenylsulfinyl, 4-methylphenylsulfinyl or naphthylsulfinyl group.

According to the invention a phosphono group is to be understood as being a P(O)(OH)$_2$ group or an ester thereof, for example the phosphonodimethyl ester, the phosphonodiethyl ester, the phosphonodiphenyl ester or the phosphonodibenzyl ester.

The term "halogen atom" includes a fluorine, chlorine, bromine or iodine atom.

The term "pseudohalogen" includes cyanates, thiocyanates (rhodanides), azides and cyanides.

The process according to the invention results in compounds of formula I of high chemical purity and high isomeric purity in a high yield, "isomeric purity" in the case of 4-methyl-7-aminoquinolones, for example, being understood as the ratio of 4-methyl-7-aminoquinolone to 4-methyl-5-aminoquinolone. For example, the process according to the invention in the case of 4-methyl-6-chloro-7-aminoquinolone results in a crude product having an isomeric purity of more than 95% in a yield of up to 96%. After customary purification, for example recrystallisation from ethanol, the yield is 90% and the isomeric purity is greater than or equal to 98%.

The present invention therefore relates also to compounds of the general formula

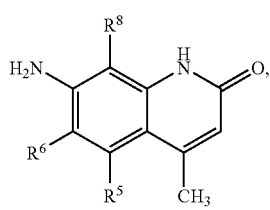
(I)

(I) especially 4-methyl-6-chloro-7-aminoquinolone or 4-methyl-6-sulfo-7-aminoquinolone, wherein $R^5$, $R^6$ and $R^8$ are each independently of the others a hydrogen atom, a nitro group, a sulfo group, a halogen atom, a pseudohalogen, a group $COOR^1$ or $CONHR^2$, a $C_{1-8}$alkyl, $C_{1-8}$alkoxy, or aryloxy radical, an amide group, a thioalkyl or thioaryl radical, an alkyl- or aryl-sulfonyl radical, an alkyl- or aryl-sulfinyl radical, a tri-fluoromethyl group or a phosphono group, $R^1$ and $R^2$ being a hydrogen atom, a $C_{1-8}$alkyl radical or an aryl or aralkyl radical, which are characterised by an isomeric purity of more than 95%, especially greater than or equal to 98%.

The compounds of formula II used as starting material for the ring-closure reaction can in principle be obtained by reaction of 1,3-diaminobenzene or a derivative thereof with diketene in aqueous solution analogously to the process described in DE-C-749 975, but the procedures described below are preferred.

The compounds of formula II in which $R^{10}$ is a group —C(O)CH$_2$C(O)CH$_3$ and $R^{11}$ is a hydrogen atom are obtained by reaction of 1 mol of a compound of formula

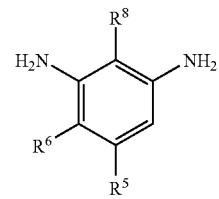
(III)

with from 1 to 1.5 mol, especially from 1.1 to 1.3 mol. of diketene of formula

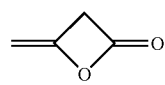
(IV)

or with from 1 to 1.5 mol, especially from 1.1 to 1.3 mol, of an ester of formula

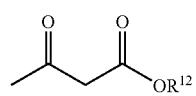
(V)

or with from 1 to 1.5 mol, especially from 1.1 to 1.3 mol, of 2,2,6-trimethyl-4H-1,3-dioxin-4-one

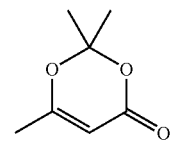

in an aqueous or organic solvent, preferably an organic solvent, most preferred an aprotic organic solvent, wherein $R^5$, $R^6$ and $R^8$ are as defined above and $R^{12}$ is a $C_{1-6}$alkyl radical, an aryl radical, such as a phenyl group, or an aralkyl radical, such as a benzyl group.

The compounds of formula II In which $R^{10}$ is a group —C(O)CH$_2$C(O)CH$_3$ and $R^{11}$ is an acyl radical are obtained correspondingly by reaction of a compound of formula

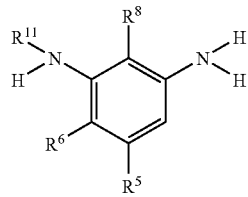
(VII)

(VII) wherein $R^5$, $R^6$ and $R^8$ are as defined above and $R^{11}$ is an acyl radical.

The compounds of formula II in which $R^{10}$ and $R^{11}$ are a group —C(O)CH$_2$C(O)CH$_3$ are obtained by reaction of 1 mol of a compound of formula

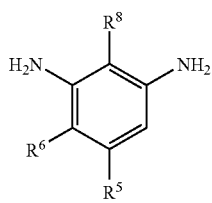

(III)

with from 2 to 3 mol, especially from 2.1 to 2.5 mol, of diketene of formula

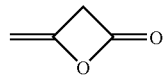

(IV)

or with from 2 to 3 mol, especially from 2.1 to 2.5 mol, of an ester of formula

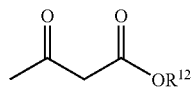

(V)

or with from 2 to 3 mol, especially from 2.1 to 2.5 mol, of 2,2,6-trimethyl-4H-1,3-dioxin-4-one

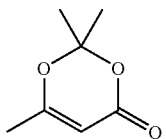

in in an aqueous or organic solvent, preferably an organic solvent, most preferred an aprotic organic solvent, wherein $R^5$, $R^6$, $R^8$ and $R^{12}$ are as defined above.

As regards the aprotic solvent, the above definition and preferences apply. If the compound of formula III is reacted with diketene, the reaction is carried out generally at from 0 to 60° C., preferably from 20 to 40° C., especially at ambient temperature. In the case of the reaction with acetoacetic acid ester or 2,2,6-trimethyl-4H-1,3-dioxin-4-one, the temperature is generally from 80 to 170° C., especially from 100 to 140° C.

The product of formula II can be isolated, optionally purified, and then converted into a compound of formula I. Preferably, however, the strong organic acid or the ammonium salt of the strong organic acid is added to an "intermediate" of formula II in the aprotic organic solvent and the "intermediate" of formula II is converted in situ into a compound of formula I. That is to say, according to the invention it is preferred that the conversion of a compound of formula III into a compound of formula II and of the resulting compound of formula II into a compound of formula I is carried out as a "one-pot reaction".

The compounds of formula II used in the process according to the invention or occurring therein as intermediates are novel and enable the desired compounds of formula I to be synthesised in a high yield, high isomeric purity and high chemical purity. The present invention therefore relates also to compounds of formula

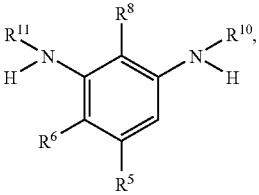

(II)

wherein $R^5$, $R^6$ and $R^8$ are each independently of the others a hydrogen atom, a nitro group, a sulfo group, a halogen atom, a pseudohalogen, a group $COOR^1$ or $CONHR^2$, a $C_{1-8}$alkyl, $C_{1-8}$alkoxy or aryloxy radical, an amide group, a thioalkyl or thioaryl radical, an alkyl- or aryl-sulfonyl radical, an alkyl- or aryl-sulfinyl radical, a trifluoromethyl group or a phosphono group, $R^1$ and $R^2$ being a hydrogen atom, a $C_{1-8}$alkyl radical or an aryl or aralkyl radical, and $R^{10}$ is a group —$C(O)CH_2C(O)CH_3$ and $R^{11}$ is a hydrogen atom or an acyl radical or $R^{10}$ and $R^{11}$ are a group —$C(O)CH_2C(O)CH_3$.

Preferably $R^{10}$ is a group —$C(O)CH_2C(O)CH_3$ and $R^{11}$ is a hydrogen atom.

Also preferred are compounds wherein at least one of the substituents $R^5$, $R^6$ and $R^8$ is other than a hydrogen atom, wherein, when $R^5$ and $R^8$ are a hydrogen atom, $R^6$ is a fluorine atom, a bromine atom, an iodine atom, a pseudohalogen, a group $COOR^1$ or $CONHR^2$, a $C_{1-8}$alkyl radical, especially a $C_{2-8}$alkyl radical, a $C_{1-8}$alkoxy radical, especially a $C_{2-8}$alkoxy radical, or an aryloxy radical, an amide group, a thioalkyl or thioaryl radical, an alkyl- or aryl-sulfonyl radical, an alkyl- or aryl-sulfinyl radical, a trifluoromethyl group or a phosphono group, wherein $R^8$ is other than a hydrogen atom, wherein $R^5$ is other than a hydrogen atom and a methyl group.

The compounds of formula II listed below are most preferred:

| Compound | $R^5$ | $R^6$ | $R^8$ | $R^{10}$ | $R^{11}$ |
|---|---|---|---|---|---|
| B1 | H | Cl | H | $C(O)CH_2C(O)CH_3$ | H |
| B2 | H | $CH_3$ | H | $C(O)CH_2C(O)CH_3$ | H |
| B3 | H | H | $CH_3$ | $C(O)CH_2C(O)CH_3$ | H |
| B4 | H | $OCH_3$ | H | $C(O)CH_2C(O)CH_3$ | H |
| B5 | H | $CO_2CH_3$ | H | $C(O)CH_2C(O)CH_3$ | H |
| B6 | COOH | H | H | $C(O)CH_2C(O)CH_3$ | H |
| B7 | $CF_3$ | H | H | $C(O)CH_2C(O)CH_3$ | H |
| B8 | $SO_3H$ | H | $CH_3$ | $C(O)CH_2C(O)CH_3$ | H |

The compounds of formula I are starting materials, important as diazo components, for the preparation of azo pigments (see, for example, DE-A-29 05 937 and PCT/EP01/12178), the compounds of formula I being reacted with suitable coupling components to form compounds of formula

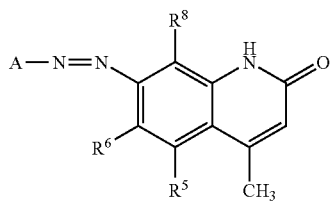
(VI)

wherein $R^5$, $R^6$ and $R^8$ are as defined above and A is the radical of a coupling component.

The conversion of compounds of formula I into compounds of formula VI comprises diazotisation and coupling.

The diazotisation of a compound of formula I is carried out, for example, with a nitrite, for example an alkali metal nitrite, such as sodium nitrite, in a medium containing a mineral acid, for example in a medium containing hydrochloric acid, generally at temperatures of from −5 to 40° C., preferably from −5 to 10° C.

The azo coupling reaction consists of the electrophilic substitution reaction of the diazonium compound with a nucleophilic partner (coupling component).

The coupling to the coupling component is effected in a manner known per se, at acidic or neutral to weakly alkaline pH values, for example a pH value of from 1 to 10, and temperatures of, for example, from −5 to 40° C., preferably from 0 to 30° C.

The process according to the invention is advantageously carried out by slowly adding a freshly prepared solution or suspension of the diazotised compound to a weakly acidic to neutral solution or suspension of the coupling component, the pH being maintained in the neutral range, for example at from pH 4.5 to 8, by addition of an aqueous alkali metal hydroxide solution, such as sodium hydroxide solution, then stirring the resulting pigment suspension until the reaction is complete and isolating the production by filtration.

Coupling components for azo pigments are generally aromatic systems having nucleophilic centres at the aromatic nucleus, especially naphthols or enolisable compounds having reactive methylene groups (see, for example, Azoic Coupling Components in Colour Index, 3rd Edition, Vol. 4, The Society of Dyers and Colorists, 1971, pp 4355–4364, 37500–37625), the coupling component preferably being selected from the following groups:

a) methylene-active compounds of the

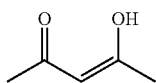

type, especially acetoacetic acid arylides;

b) 2-hydroxynaphthalene and 3-carboxylic acid derivatives thereof, for example 2'-hydroxy-3'-naphthoylanilines (naphthol AS derivatives);

c) pyrazolone derivatives, especially pyrazolone derivatives of formula

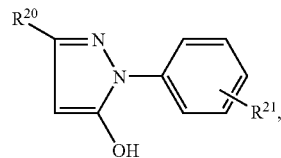

wherein $R^{20}$ is a $C_{1-4}$alkyl radical, especially a methyl group, or a group $COOR^1$, $R^1$ being as defined above, especially a methyl or ethyl ester group, and $R^{21}$ being a hydrogen atom, a halogen atom or a sulfo group or a $C_{1-4}$alkyl radical, especially a methyl group (see W. Herbst, K. Hunger, Industrielle Organische Pigmente, 2nd fully revised edition, 1995, pp 198–203).

When 4methyl-6-chloro-7-aminoquinolone (PCT/EP01/12178) having an isomeric purity greater than 95% is used for the preparation of

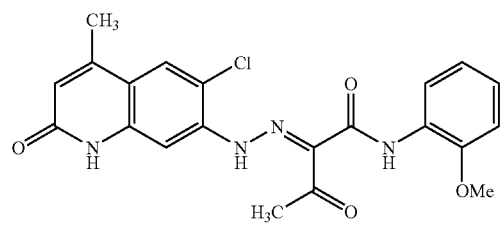

the colour shade of the resulting pigment is not red-shifted, as is the case when relatively large amounts of contaminants are present, but the pigment exhibits improved colour (chroma) and improved fastness to weathering.

The following Examples illustrate the present invention but do not limit the scope thereof. Unless otherwise indicated, isomeric purities are determined by means of HPLC taking account of the relevant response factors.

EXAMPLE 1

4-Methyl-6-chloro-7-aminoquinolone (PPTS)

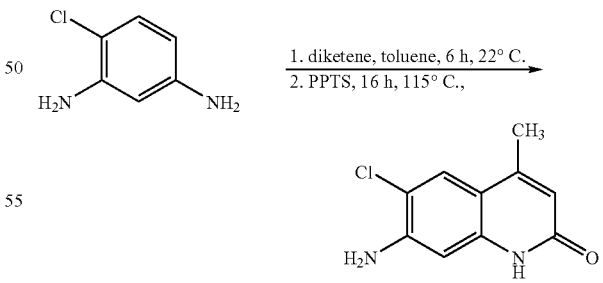

28.6 g of 4-chloro-1,3-phenylendiamine are suspended at 22° C. in 400 ml of toluene. 17.6 g of diketene in 100 ml of toluene are added to the grey suspension in the course of 30 minutes at 25±2° C., the suspension briefly passing into solution before the mono-diketenisation product is precipitated in the form of a beige solid. Stirring is then carried out for 6 h at 22° C. Then 5 g of pyridinium para-toluenesulfonate (PPTS) are added and the mixture is boiled under reflux for 16 h. The yellow suspension is cooled to 30° C., with stirring, and then at 30° C. 30 ml of 1 N NaOH are added. A further 100 ml of water are then added. The crude product is filtered at 22° C., washed neutral with $H_2O$ and dried overnight at 60° C. in vacuo. 38.5 g (yield: 92%, isomeric ratio of 4-methyl-6-chloro-7-aminoquinolone to 4-methyl-5-amino-6-chloroquinolone>95:5) of a beige solid having a melting point of 350° C. are obtained.

Recrystallisation from ethanol results in a product having an isomeric purity of from 98 to 99% and a melting point of 358° C. in a yield of 90%.

EXAMPLE 2

4-Methyl-6-chloro-7-aminoquinolone (TsOH)

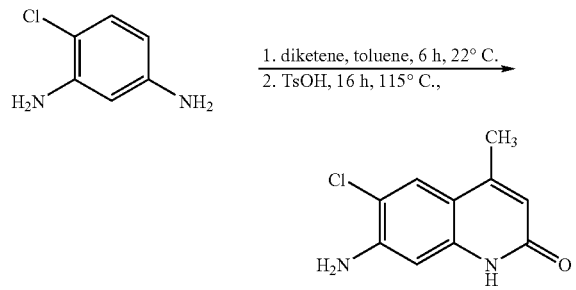

90.5 g of 4-chloro-1,3-phenylenediamine moistened with water (dry weight: 54.4 g) are introduced into 850 ml. of toluene in a 2.5 liter sulfonating flask having a KPG (calibrated precision glass) stirrer, internal thermometer, water separator with a reflux condenser and a bubble counter, and the brown suspension is boiled under reflux, with vigorous stirring, while at the same time about 36 ml of residual water is removed azeotropically. The mixture is cooled to room temperature and at an internal temperature of 25±2° C. a solution of 38.3 g of diketene in 100 ml of toluene is added to the grey suspension in the course of 30 minutes, the suspension briefly passing into solution before the adduct is precipitated in the form of a beige solid.

Stirring is carried out for 6 h at 22° C. 7.6 g of p-toluenesulfonic acid monohydrate are then added and the mixture is boiled under reflux for 16 h, about 6 ml of water being isolated. The dark-yellow suspension is cooled, with stirring, and then at 30° C. 48 ml of 1 N NaOH are added. 200 ml of water are then added and stirring is carried out for 2 hours. The grey crude product is filtered at 22° C., washed neutral with $H_2O$ and dried overnight at 60° C. in vacuo. 73.8 g (yield: 93%, isomeric ratio of 4-methyl-6-chloro-7-aminoquinolone to 4-methyl-5-amino-6-chloroquinolone=97:3) of a beige solid are obtained.

Recrystallisation from ethanol results in a product having an isomeric purity of >98% and a melting point of 358° C. in a yield of 90%.

The following Table shows the effect of contaminants on the quality of the prepared pigments with specific reference to the azo pigment synthesised according to PCT/EP01/12178 (Example 1) illustrated below:

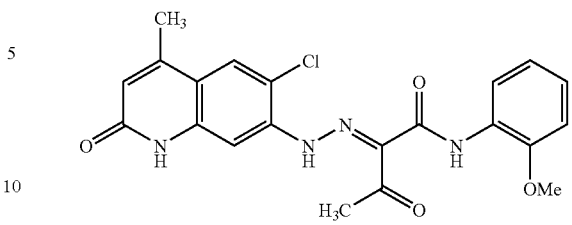

| Masstone (5% coloured pigment in an AM standard coating) | | Fastness to overspraying | Fastness to weathering after 1000 h | Contamination[1] |
|---|---|---|---|---|
| Chroma | Hue | 30 min./130° C. | ΔE | % |
| 83.9 | 94.5 | 4.8 | 2.9 | not detectable |
| 82.4 | 95.2 | 4.6 | 3.0 | 1–2 |
| 81.8 | 95.8 | 4.6 | 4.1 | 5 |
| 79.4 | 93.9 | 4.7 | 7.0 | 18 |
| 76.7 | 93.3 | 4.6 | 8.3 | 22 |

[1]Isomeric contaminant (4-methyl-5-amino-6-chloroquinolone) in the starting material (4-methyl-6-chloro-7-aminoquinolone) according to HPLC analysis.

It can be seen from the Table that increased amounts of contaminants result in the pigment colour shade being markedly red-shifted. In addition to the red shift, higher levels of contaminants result in a pigment having poorer colour (chroma) and poorer fastness to weathering.

EXAMPLE 3

Preparation of the pyridinium salt of 4-methyl-6-sulfo-7-aminoquinolone

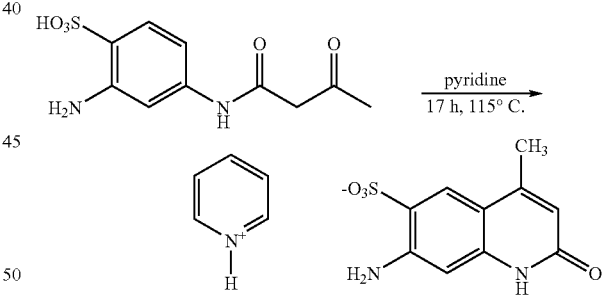

27.23 g of 2-amino-4-acetoacetamidobenzenesulfonic acid are stirred in 150 ml of pyridine and the brownish-yellow suspension is boiled under reflux. After 17 h the greenish suspension is cooled, with stirring, to 70° C. and the mixture is concentrated to dryness under a water-jet vacuum. The green solid is taken up at 25° C. in 60 ml of methanol, filtered and washed first with methanol, then with water and dried overnight at 60° C. in vacuo. 26.4 g (yield: 79%, isomeric ratio of 4-methyl-6-sulfo-7-aminoquinolone pyridinium salt to 4-methyl-5-amino-6-sulfoquinolone pyridinium salt >96.1:3.9) of a beige solid having a melting point of 235° C. are obtained.

The isomerically pure aminoquinolonesulfonic acid can be obtained from the pyridinium salt by dissolution in boiling acetic acid, cooling to 25° C. and subsequent filtration. After drying in vacuo, 95% of a white solid having a melting point of 362° C. (DE-A-95 86 47: 340–350° C., decomposition) are obtained.

EXAMPLE 4

28.6 g of 4-chloro-1,3-phenylenediamine are suspended at 22° C. in 400 ml of toluene. 17.6 g of diketene in 100 ml of toluene are added to the grey suspension in the course of 30 minutes at 25±2° C., the suspension briefly passing into solution before the mono-diketenisation product is precipitated in the form of a beige solid. The reaction mixture is stirred for 6 h at 22° C., then cooled to 10° C., filtered and washed with toluene. The filter cake is dried overnight at 60° C. in vacuo. 44.6 g (yield: 98%) of a beige solid having a melting point of 106° C. are obtained.

EXAMPLES 5 TO 46

906.6 mg (4 mmol) of N-(3-amino-4-chloro-phenyl)-acetoacetamide and 0.4 mmol of catalyst are introduced into 8 ml of solvent. The solution or suspension is heated at 100° C., with stirring, for 16 h. The resulting suspension is cooled to 70° C.; 3 ml of absolute ethanol are added and the suspension is heated under reflux for 2 h. The suspension is cooled to room temperature, filtered and washed with 2 ml of absolute ethanol and again with 1 ml of absolute ethanol, then with 20 ml of water and the resulting residue is dried overnight at 60° C. in vacua. The dried product is analysed by means of HPLC (High-Performance Liquid Chromatography) by comparison with authentic samples.

The yields and product distributions obtained with various solvents and catalysts are listed in Table 1.

TABLE 1

| Example | Solvent | Catalyst | Yield [%] | Product A [%] | Product B [%] | Product C [%] |
|---|---|---|---|---|---|---|
| 5 | dibutyl ether | pyridinium tetrafluoroborate | 94.6 | 97.5 | 2.3 | 0.2 |
| 6 | dibutyl ether | pyridinium p-toluenesulfonate | 94.1 | 96.6 | 3.0 | 0.3 |
| 7 | dibutyl ether | p-toluenesulfonic acid | 93.5 | 95.1 | 4.5 | 0.4 |
| 8 | toluene | pyridinium tetrafluoroborate | 93.4 | 98.1 | 1.7 | 0.2 |
| 9 | benzine (boiling range 110–140° C.) | pyridinium p-toluenesulfonate | 93.4 | 96.9 | 3.0 | 0.1 |
| 10 | dibutyl ether | iodine | 93.2 | 97.3 | 2.5 | 0.1 |
| 11 | dibutyl ether | sodium hydrogen sulfate hydrate | 93.2 | 94.3 | 5.3 | 0.3 |
| 12 | dibutyl ether | dodecylbenzenesulfonic acid/pyridine 1:1 | 92.8 | 95.3 | 4.2 | 0.4 |
| 13 | dibutyl ether | pyridinium dodecylbenzenesulfonate | 92.7 | 95.1 | 4.3 | 0.5 |
| 14 | decahydronaphthalene | pyridinium p-toluenesulfonate | 92.7 | 96.8 | 3.0 | 0.2 |
| 15 | dibutyl ether | pyridine/$SO_3$ adduct | 92.0 | 94.5 | 5.2 | 0.3 |
| 16 | dibutyl ether | zinc chloride (anhydrous) | 91.4 | 98.1 | 1.4 | 0.4 |
| 17 | Dowtherm ® A | pyridinium p-toluenesulfonate | 91.3 | 96.1 | 3.6 | 0.3 |
| 18 | dibutyl ether | iron(III) chloride (anhydrous) | 91.1 | 97.0 | 2.5 | 0.5 |
| 19 | toluene | pyridine/$SO_3$ adduct | 91.1 | 95.8 | 4.1 | 0.1 |
| 20 | toluene | iron(III) chloride (anhydrous) | 90.7 | 98.0 | 1.7 | 0.3 |
| 21 | 1,2,3,4-tetrahydronaphthalene | pyridinium p-toluenesulfonate | 90.6 | 97.2 | 2.7 | 0.1 |
| 22 | toluene | sodium hydrogen sulfate hydrate | 90.5 | 95.7 | 4.0 | 0.2 |
| 23 | toluene | pyridinium p-toluenesulfonate | 90.5 | 96.7 | 3.1 | 0.2 |
| 24 | decahydronaphthalene | iodine | 89.8 | 96.8 | 3.0 | 0.2 |
| 25 | toluene | benzenesulfonic acid | 89.6 | 96.3 | 3.6 | 0.1 |
| 26 | dibutyl ether | dodecylbenzenesulfonic acid | 89.2 | 96.0 | 3.6 | 0.3 |
| 27 | decahydronaphthalene | dodecylbenzenesulfonic acid | 88.8 | 95.1 | 4.4 | 0.5 |
| 28 | 1,2-propylene carbonate | pyridinium p-toluenesulfonate | 88.6 | 96.5 | 3.4 | 0.1 |
| 29 | dibutyl ether | 0.5 p-toluenesulfonic anhydride | 88.6 | 96.4 | 3.3 | 0.3 |
| 30 | toluene | iodine | 88.5 | 97.4 | 2.5 | 0.1 |
| 31 | toluene | p-toluenesulfonic acid | 88.5 | 98.1 | 1.7 | 0.1 |
| 32 | decahydronaphthalene | p-toluenesulfonic acid | 88.2 | 96.0 | 3.7 | 0.2 |
| 33 | 1,2-propylene carbonate | iodine | 87.8 | 97.8 | 2.1 | 0.1 |
| 34 | dibutyl ether | p-toluenesulfonic acid chloride | 87.8 | 96.4 | 3.5 | 0.1 |
| 35 | toluene | 0.5 p-toluenesulfonic anhydride | 87.7 | 96.6 | 3.3 | 0.1 |
| 36 | dibutyl ether | yttrium(III) trifluoromethanesulfonate | 87.3 | 99.0 | 0.7 | 0.3 |
| 37 | decahydronaphthalene | 0.5 p-toluenesulfonic anhydride | 87.1 | 96.2 | 3.6 | 0.2 |
| 38 | 1,2,3,4-tetrahydronaphthalene | iodine | 87.0 | 97.3 | 2.4 | 0.2 |
| 39 | dibutyl ether | ytterbium(III) trifluoromethanesulfonate | 86.5 | 98.9 | 0.9 | 0.2 |
| 40 | toluene | ytterbium(III) trifluoromethanesulfonate | 86.4 | 99.2 | 0.7 | 0.1 |
| 41 | 1,2,3,4-tetrahydronaphthalene | 0.5 p-toluenesulfonic anhydride | 86.3 | 96.3 | 3.4 | 0.2 |
| 42 | toluene | yttrium(III) trifluoromethanesulfonate | 86.3 | 99.4 | 0.5 | 0.1 |

TABLE 1-continued

| | | | | Product A | Product B | Product C |
|---|---|---|---|---|---|---|
| Example | Solvent | Catalyst | Yield [%] | [%] | [%] | [%] |
| 43 | γ-butyrolactone | iodine | 80.2 | 98.8 | 1.1 | 0.1 |
| 44 | N,N-dimethylacetamide | pyridinium p-toluenesulfonate | 68.1 | 99.2 | 0.6 | 0.1 |
| 45 | N-methylpyrrolidone | pyridinium p-toluenesulfonate | 65.7 | 99.0 | 0.9 | 0.1 |
| 46 | toluene | pyridinium hydrogen sulfate | 89.7 | 93.0 | 6.9 | 0.1 |
| Comparison Example 6 | toluene | - (reference) | 16.4 | 0.1 | 0.1 | 99.8 |

COMPARISON EXAMPLE 1 (DE-A-24 44 519)

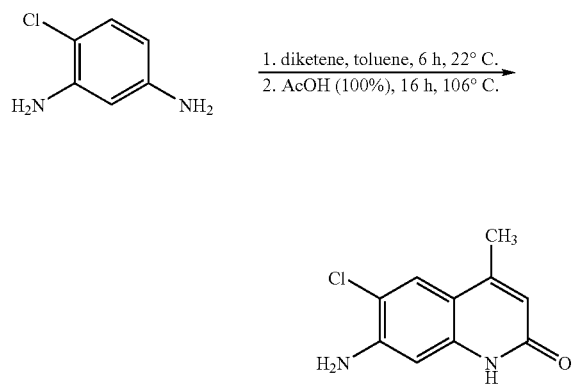

28.6 g of 4-chloro-1,3-phenylenediamine are suspended at 22° C. in 400 ml of toluene. 17.7 g of diketene in 100 ml of toluene are added to the grey suspension in the course of 30 minutes at 25±2° C., the suspension briefly passing into solution before the mono-diketenisation product is precipitated in the form of a solid. Stirring is then carried out for 6 h at 22° C. 1.2 g of AcOH (100%) are then added and the mixture is boiled under reflux for 16 h. The dark-brown sticky suspension is cooled, with stirring, to 30° C. and then at 30° C. 30 ml of 1 N NaOH are added. A further 100 ml of water and 200 ml of aqueous 25% NaCl solution are then added; the mixture is cooled to 10° C. and stirred for a further 2 h. The supernatant aqueous phase and the light-brown organic phase are decanted off and the viscous blackish-brown residue that remains is stirred with 200 ml of isopropanol. The dark, crystalline mass is filtered and constituents dissolved in the filtrate are precipitated by addition of 150 g of ice; filtration is again carried out, the combined precipitates are washed with 50 ml of water and the dark-brown crude product is dried overnight at 60° C. in vacuo. 12.5 g (yield: 30%) of a brown solid (melting point 230° C.) are obtained, which according to HPLC contains the desired 4-methyl-6-chloro-7-aminoquinolone in an amount of about 10%.

COMPARISON EXAMPLE 2 (DE-A-24 44 519)

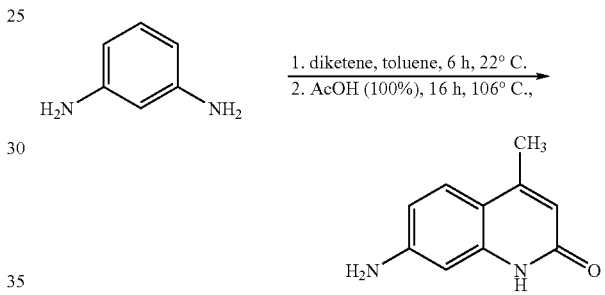

21.6 g of 1,3-phenylenediamine are suspended at 22° C. in 400 ml of toluene. 17.7 g of diketene in 100 ml of toluene are added to the grey suspension in the course of 30 minutes at 25±2° C., the suspension changing into a viscous mass. Stirring is then carried out for 6 h at 22° C.: 1.2 g of AcOH (100%) are then added and the mixture is boiled-under reflux for 16 h. The yellowish sticky suspension is cooled to 30° C., with stirring, and then at 30° C. 30 ml of 1N NaOH are added. A further 100 ml of water and 200 ml of aqueous 25% NaCl solution are then added and the mixture is cooled to 10° C. and then stirred for a further 2 h. The yellow suspension is filtered and then washed with 1500 ml of water and the deep-yellow crude product is dried overnight at 60° C. in vacuo. 31.3 g (yield: 90%) of a deep-yellow solid having a melting point of 249° C. are obtained, containing the desired 4-methyl-7-amino-quinolone in an amount of 90%. After recrystallisation from methanol, white crystals having a melting point of 280° C. are obtained.

COMPARISON EXAMPLE 3 (DE-A-958 647)

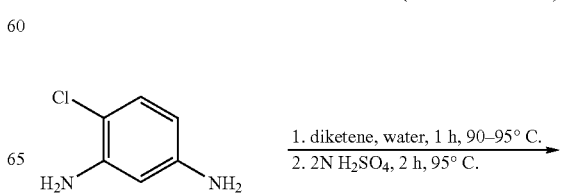

-continued

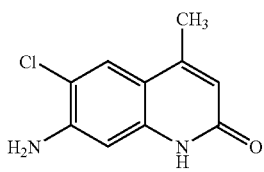

17.2 g of 95% 4-chloro-1,3-diaminobenzene are dissolved in 250 g of warm water. With stirring, 9.3 g of diketene are added dropwise in the course of 1 hour at 90–95° C., the aceto-acetyl compound being precipitated partially in oily form. After the addition of 27 g of 2N sulfuric acid, the mixture is heated at 95° C. for 2 h. The oily acetoacetyl compound rapidly changes into a fine, crystalline, dark-brown precipitate. The hot reaction mixture is neutralised with 30 ml of 2N NaOH and stirred for a further 30 minutes. The hot reaction mixture is filtered and washed neutral with 100 ml of cold water in portions. The deep-brown product is dried at 60° C. in vacuo. 18 g (yield: 78%, ratio of 4-methyl-6-chloro-7-aminoquinolone: 4-methyl-5-amino-6-chloro-quinolone: further, unidentified product=about 86:13:1) of a dark-brown solid having a melting point of 345° C. are obtained.

COMPARISON EXAMPLE 4 (DE-A-1278039)

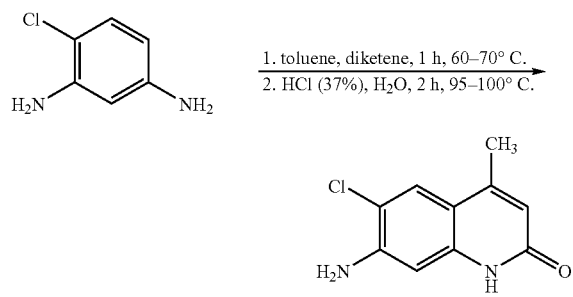

8.4 g of diketene are stirred with 15 g of toluene, and 7.2 g of 4-chloro-1,3-diaminobenzene are added at such a rate that the heat of reaction causes the temperature to rise to 60–70° C. After being stirred for one hour at 60–70° C., the mixture is cooled to 15° C. 50 g of water and 10 g of HCl (37%) are introduced into the black oil and the mixture is then distilled until a boiling temperature of 95–100° C. is reached. That temperature is maintained for 2 h. After about one hour, the black solution changes into a suspension. The greyish-green suspension is then cooled to 15° C., stirred for 30 minutes and filtered. The greyish-green filter cake is introduced into 50 g of water; 5 g of sodium acetate are added and the mixture is boiled for one hour. The mixture is then cooled to room temperature and the suspension is filtered. The grey product is washed neutral with 200 g of cold water and dried at 60° C. in vacuo. 6 g (yield: 58%, isomeric ratio of 4-methyl-6-chloro-7-aminoquinolone to 4-methyl-5-amino-6-chloroquinolone=about 53:47) of a grey solid having a melting point of 290° C. are obtained.

COMPARISON EXAMPLE 5 (DE-A-95 86 47)

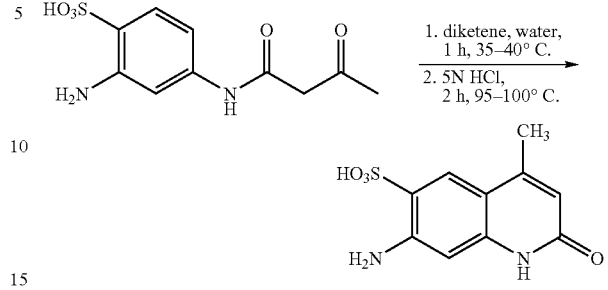

18.8 g (0.1 mol) of 4-sulfo-1,3-phenylenediamine are suspended in 150 ml of water and the suspension is heated to 35° C. 9.3 g (0.11 mol) of diketene are added to the grey suspension in the course of 60 minutes at 35–40° C. The mixture is heated to 92° C. in the course of 30 min; 4 g of 5N HCl are then added to the yellowish-green suspension and the mixture is boiled under reflux for a further 2 h. A further 33 g of 5N HCl are then added. The suspension is cooled to 22° C., filtered and washed with a total of 150 ml of cold water In portions. The grey product is dried overnight at 60° C. in vacuo. 9 g (yield 35%; ratio of 4-methyl-6-sulfo-7-aminoquinolone: 4-methyl-5-amino-6-sulfoquinolone: further, unidentified product=71:21:8) of a beige solid having a melting point of 288° C. are obtained.

What is claimed is:
1. A process for the preparation of a compound of the formula

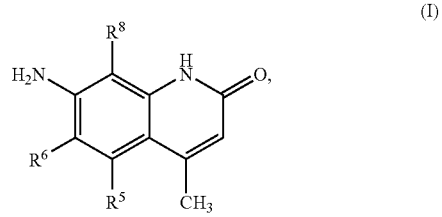

which comprises converting a compound of the formula

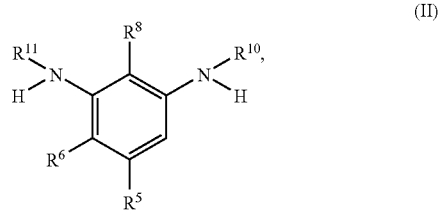

in an aprotic organic solvent in the presence of a catalytically active amount of a strong acid (catalyst) or of an agent that liberates a strong acid or of an ammonium salt of a strong acid, it also being possible for the catalyst to be part of the starting material/product, into a compound of formula I, wherein $R^5$, $R^6$ and $R^8$ are each independently of the others a hydrogen atom, a nitro group, a sulfo group, a halogen atom, a pseudohalogen, a group $COOR^1$ or CONHR², a C₁₋₈alkyl, C₁₋₈alkoxy or aryloxy radical, an amide group, a thioalkyl or thioaryl radical, an alkyl- or aryl-sulfonyl radical, an alkyl- or aryl-sulfinyl radical, a trifluoromethyl group or a phosphono group, R¹ and R² being a hydrogen atom or a C₁₋₈alkyl radical or an aryl or aralkyl radical, R¹⁰ is a group —C(O)CH₂C(O)CH₃ and R¹¹ is a hydrogen atom or an acyl radical, or R¹⁰ and R¹¹ are a group —C(O)CH₂C(O)CH₃.

2. A process according to claim 1, wherein a compound of formula II in which R¹⁰ is a group —C(O)CH₂C(O)CH₃ and R¹¹ is a hydrogen atom is obtained by reaction of 1 mol of a compound of formula

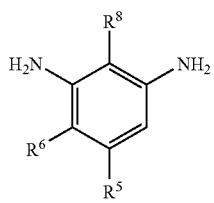
(III)

with from 1 to 1.5 mol of diketene of formula

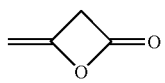
(IV)

or with from 1 to 1.5 mol of an ester of formula

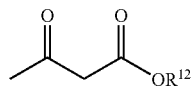
(V)

or with from 1 to 1.5 mol of 2,2,6-trimethyl-4H-1,3-dioxin-4-one, in an aqueous or organic solvent, wherein R⁵, R⁶ and R⁸ are as defined in claim 1 and R¹² is a C₁₋₆alkyl radical, an aryl radical or an aralkyl radical.

3. A process according to claim 1, wherein a compound of formula II in which R¹⁰ and R¹¹ are a group —C(O)CH₂C(O)CH₃ is obtained by reaction of 1 mol of a compound of formula

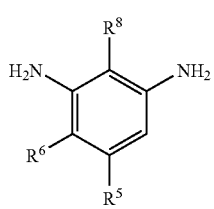
(III)

with from 2 to 3 mol of diketene of formula

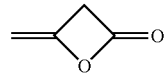
(IV)

or with from 2 to 3 mol of an ester of formula

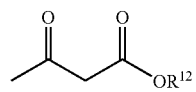
(V)

or with from 2 to 3 mol of 2,2,6-trimethyl-4H-1,3-dioxin-4-one, in an aqueous or organic solvent, wherein R⁵, R⁶ and R⁸ are as defined in claim 1 and R¹² R¹² is a C₁₋₆alkyl radical, an aryl radical or an aralkyl radical.

4. A process according to claim 1, wherein the conversion of a compound of formula II into a compound of formula I is carried out at a temperature of from 20 to 200° C.

5. A process according to claim 1, wherein R⁶ is a sulfo group, a halogen atom or pseudohalogen.

6. A process according to claim 1, wherein R⁵ and R⁸ are a hydrogen atom.

7. A process according to claim 1, wherein the aprotic organic solvent is selected from the group consisting of diethyl ether, methyl ethyl ether, di-n-propyl ether, diisopropyl ether, methyl n-butyl ether, methyl tert-butyl ether, ethyl n-propyl ether, di-n-butyl ether, tetrahydrofuran, 1,4-dioxane, 1,2-dimethoxyethane, bis-β-methoxyethyl ether; anisole, phenetole; diphenyl ether, ditolyl ether; hexane, heptane, low- or high-boiling petroleum ethers; cyclohexane, methylcyclohexane, decahydronaphthalene; benzene, toluene, o-, m- or p-xylene, ethylbenzene, 1,2,3,4-tetrahydro-naphthalene, biphenyl; methylene chloride, chloroform, carbon tetrachloride, chlorobenzene, dichlorobenzene; n-butyl acetate, 1,2-propylene carbonate, γ-butyrolactone; N,N-dimethylformamide, N, N-dimethylacetamide, N-methylpyrrolidone and mixtures of such solvents.

8. A process according to claim 1, wherein the catalyst is selected from pyridinium p-toluenesulfonate (PPTS), pyridinium dodecylbenzenesulfonate, pyridinium tetrafluoroborate, pyridinium hydrogen sulfate, pyridine/SO₃ complex, p-toluenesulfonic acid, benzenesulfonic acid, dodecylbenzenesulfonic acid, p-toluenesulfonic acid chloride, p-toluenesulfonic anhydride, benzoyl chloride, 2,4,6-trimethylbenzoyl chloride, sulfuric acid, amidosulfuric acid (sulfamic acid), sodium hydrogen sulfate, anhydrous zinc chloride, anhydrous iron(III) chloride, anhydrous aluminium chloride, scandium(III) trifluoromethanesulfonate, yttrium(III) trifluoromethanesulfonate, ytterbium(III) trifluoromethanesulfonate and iodine.

9. A process according to claim 3, wherein the conversion of a compound of formula III into a compound II and of the resulting compound of formula II into a compound of formula I is carried out as a one-pot reaction.

10. A process according to claim 1, wherein a compound of formula I is reacted with a suitable coupling component to form a compound of formula

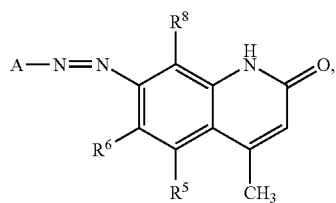

(VI)

$R^5$, $R^6$ and $R^8$ being as defined in claim 1 and A being the radical of a coupling component.

11. A compound of the formula

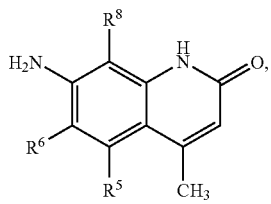

(I)

wherein $R^5$, $R^6$ and $R^8$ are each independently of the others a hydrogen atom, a nitro group, a sulfo group, a halogen atom, a pseudohalogen, a group $COOR^1$ or $CONHR^2$ or a $C_{1-8}$alkyl, $C_{1-8}$alkoxy or aryloxy radical, an amide group, a thioalkyl or thioaryl radical, an alkyl- or aryl-sulfonyl radical, an alkyl- or aryl-sulfinyl radical, a trifluoromethyl group or a phosphono group, $R^1$ and $R^2$ being a hydrogen atom, a $C_{1-8}$alkyl radical or an aryl or aralkyl radical, having an isomeric purity of more than 95%.

* * * * *